(12) United States Patent
Chouzier et al.

(10) Patent No.: US 11,306,052 B2
(45) Date of Patent: Apr. 19, 2022

(54) CYCLOALKANE OXIDATION CATALYSTS AND METHOD TO PRODUCE ALCOHOLS AND KETONES

(71) Applicant: Performance Polyamides, SAS, Paris (FR)

(72) Inventors: Sandra Chouzier, Lyons (FR); Fabien Ocampo, La Courneuve (FR); Sergio Mastroianni, Lyons (FR); Avelino Corma, Valencia (ES); Mercedes Boronat, Valencia (ES); Javier Tirso Lopez Ausens, Sabiñanigo (ES)

(73) Assignee: Performance Polyamides, SAS, Lyons (FR)

( * ) Notice: Subject to any disclaimer, the term of this patent is extended or adjusted under 35 U.S.C. 154(b) by 87 days.

(21) Appl. No.: 15/538,582

(22) PCT Filed: Dec. 18, 2015

(86) PCT No.: PCT/EP2015/080410
§ 371 (c)(1),
(2) Date: Jun. 21, 2017

(87) PCT Pub. No.: WO2016/102343
PCT Pub. Date: Jun. 30, 2016

(65) Prior Publication Data
US 2017/0349524 A1 Dec. 7, 2017

(30) Foreign Application Priority Data
Dec. 22, 2014 (EP) .................................. 14290400

(51) Int. Cl.
| | | |
|---|---|---|
| C07C 51/31 | (2006.01) | |
| C07C 45/28 | (2006.01) | |
| C07C 29/48 | (2006.01) | |
| C07C 29/132 | (2006.01) | |
| C07C 45/53 | (2006.01) | |
| C07C 407/00 | (2006.01) | |
| C08G 69/28 | (2006.01) | |

(52) U.S. Cl.
CPC .......... *C07C 51/316* (2013.01); *C07C 29/132* (2013.01); *C07C 29/48* (2013.01); *C07C 45/28* (2013.01); *C07C 45/53* (2013.01); *C07C 407/00* (2013.01); *C08G 69/28* (2013.01); *C07C 2601/14* (2017.05)

(58) Field of Classification Search
CPC .......... C07C 29/48; C07C 2/66; C07C 45/53; C07C 51/31; C08G 69/28
See application file for complete search history.

(56) References Cited

U.S. PATENT DOCUMENTS

| | | | |
|---|---|---|---|
| 2,359,833 A | 10/1944 | Faris et al. | |
| 2,439,513 A | 4/1948 | Hamblet et al. | |
| 6,214,306 B1* | 4/2001 | Aubert | B01D 53/945 423/213.2 |
| 6,677,490 B2 | 1/2004 | Clark et al. | |
| 6,995,233 B2 | 2/2006 | Thierry et al. | |
| 2003/0097025 A1* | 5/2003 | Clark | B01J 31/1633 568/385 |
| 2004/0073061 A1 | 4/2004 | Kawase et al. | |
| 2005/0070742 A1 | 3/2005 | Ishida et al. | |
| 2006/0210462 A1 | 9/2006 | Larcher et al. | |
| 2006/0224020 A1* | 10/2006 | Corma | B01J 23/66 568/360 |
| 2012/0316059 A1 | 12/2012 | Ohtake et al. | |
| 2014/0256981 A1 | 9/2014 | Narisawa et al. | |
| 2014/0296578 A1 | 10/2014 | Notestein et al. | |

FOREIGN PATENT DOCUMENTS

| | | | |
|---|---|---|---|
| EP | 0300852 | A1 | 1/1989 |
| EP | 0388567 | A1 | 9/1990 |
| EP | 1435338 | A1 | 7/2004 |
| EP | 1518849 | A1 | 3/2005 |
| FR | 2744719 | * | 8/1997 |
| GN | 101036887 | A | 9/2007 |
| JP | 2003-517030 | A | 5/2003 |
| JP | 2004-010520 | A | 1/2004 |
| JP | 2005-104857 | A | 4/2005 |
| JP | 2007-223933 | A | 9/2007 |
| JP | 2008-189588 | A | 8/2008 |
| RU | 2233830 | C2 | 8/2004 |
| WO | 01/44153 | A1 | 6/2001 |
| WO | 02/059071 | A1 | 8/2002 |
| WO | WO 030099755 | * | 12/2003 |
| WO | 2013/008637 | A1 | 1/2013 |
| WO | 2014015491 | A1 | 1/2014 |

(Continued)

OTHER PUBLICATIONS

Pires et al (Effects of oxidant and solvent on the liquid-phase cyclohexane oxidation catalyzed by Ce-exchanged zeolite Y, Applied Catalysis A: General 203 (2000) 231-237), published on Mar. 2000.*

Yao et al (Liquid-Phase (Cooxidation of Cyclohexane and Cyclohexanone over Supported Cerium Oxide Catalysts. Ind. Eng. Chem. Res. 1998, 37, 2647-2653), published on Dec. 1998.*

S. Laursen et al., "First-Principles Design of Highly Active and Selective Catalysts for Phosgene-Free Synthesis of Aromatic Polyurethanes**," Angew. Chem. Int. Ed. 2012, No. 51, pp. 4190-4193 (4 pages).

(Continued)

*Primary Examiner* — Gregory Listvoyb

(74) *Attorney, Agent, or Firm* — Osha Bergman Watanabe & Burton LLP

(57) ABSTRACT

The present invention concerns a method of oxidizing a cycloalkane to form a product mixture containing a corresponding alcohol and ketone, said method comprising contacting a cycloalkane with a hydroperoxide compound in the presence of a catalytic effective amount of a cerium oxide based catalyst.

12 Claims, No Drawings

(56) References Cited

FOREIGN PATENT DOCUMENTS

WO    2014/170422  A1   10/2014
WO     2014202725  A1   12/2014

OTHER PUBLICATIONS

H.X. Mai et al., "Shape-Selective Synthesis and Oxygen Storage behavior of Ceria Nanopolyhedra, Nanorods, and Nanocubes," J. Phys. Chem., B 2005, No. 109, pp. 24380-24385 (6 pages).
International Search Report issued in corresponding International Application No. PCT/EP2015/080410; dated Feb. 25, 2016 (4 pages).
Written Opinion of the International Search Authority issued in corresponding International Application No. PCT/EP2015/080410; dated Feb. 25, 2016 (7 pages).
Office Action issued in Japanese Application No. 2017-533609, dated Dec. 9, 2019 (10 pages).
M. Tsuruta, "Polyamide Synthetic Fiber", Journal of Synthetic Organic Chemistry, 1963, vol. 21, No. 3, p. 216-227 (12 pages).
Office Action issued in Chinese Application No. 201580070463.8, dated Mar. 2, 2020 (12 pages).
Search Report issued in Chinese Application No. 201580070463.8, dated Mar. 2, 2020 (2 pages).
Li Feng-Jiao et al., "Synthetic and Modifying Technology of Polyamide", Plastics, vol. 43, No. 4, pp. 72-75 (4 pages).

\* cited by examiner

CYCLOALKANE OXIDATION CATALYSTS AND METHOD TO PRODUCE ALCOHOLS AND KETONES

This application is a U.S. national phase entry under 35 U.S.C. § 371 of International Application No. PCT/EP2015/080410, filed Dec. 18, 2015, which claims priority to EP 14290400.2 filed on Dec. 22, 2014. The entire content of each of these applications is hereby incorporated herein by reference.

The present invention concerns a method of oxidizing a cycloalkane to form a product mixture containing a corresponding alcohol and ketone, said method comprising contacting a cycloalkane with a hydroperoxide compound in the presence of a catalytic effective amount of a cerium oxide based catalyst.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Several different processes have been used for the oxidation of cyclohexane into a product mixture containing cyclohexanone and cyclohexanol. Such product mixture is commonly referred to as a KA oil (ketone/alcohol oil) mixture. The KA oil mixture can be readily oxidized to produce adipic acid, which is an important reactant in processes for preparing certain condensation polymers, notably polyamides. Given the large quantities of adipic acid consumed in these and other processes, there is a need for cost-effective processes for producing adipic acid and its precursors.

Classical process to produce a mixture containing cyclohexanone and cyclohexanol is conducted in two steps to get KA oil through oxidation of cyclohexane. First, the thermal auto-oxidation of cyclohexane leads to the formation of cyclohexyl hydroperoxide (CyOOH) that is isolated. The second step, KA oil is obtained through the decomposition of CyOOH which is catalyzed by using chromium ions or cobalt ions as homogenous catalysts.

With the regulation restrictions all over the world, the requirement of replacement of environmentally unfriendly catalysts, such as chromium and cobalt catalysts, becomes more and more urgent. The environmental footprint and the economics of this process could be significantly improved if the current homogeneous catalysts could be replaced by non-toxic catalysts.

Various types of homogeneous catalysts have been used to catalyze oxidation of cyclohexane by hydroperoxide to produce KA oil.

Heterogeneous catalysts processes have the advantage of easy separation and have been reported to catalyze the oxidation of cyclohexane by hydroperoxide. Many heterogeneous catalysts are based on zeolite-like supports in which transition metals or noble metals are incorporated or implemented, or on oxide supports on which transition metals are deposited.

There remains a need of a heterogeneous catalyst with high oxidation ability to get high conversion of cyclohexane and high selectivity to KA oil with low cost of catalyst preparation.

INVENTION

It appears now that it's perfectly possible to produce a mixture of alcohol and ketone from a cycloalkane with a high oxidation ability, high selectivity to KA oil with a good compromise of conversion and yield. Such results can be obtained with the use of a catalytic effective amount of a cerium oxide based catalyst that showed a high oxidation ability.

The present invention then concerns a method of oxidizing a cycloalkane to form a product mixture containing a corresponding alcohol and ketone, said method comprising contacting a cycloalkane with a hydroperoxide compound in the presence of at least a cerium oxide based catalyst.

The invention also concerns a method to produce adipic acid comprising one step being the present method oxidizing a cycloalkane.

The invention also concerns a method to produce a polyamide from adipic acid and hexamethylene diamine, the adipic acid being obtained by the method to produce adipic acid of the invention.

Other characteristics, details and advantages of the invention will emerge even more fully upon reading the description which follows.

Throughout the description, including the claims, the term "comprising one" should be understood as being synonymous with the term "comprising at least one", unless otherwise specified, and "between" should be understood as being inclusive of the limits.

Cycloalkane

Cycloalkane may refer to saturated cyclic hydrocarbons having from 3 to about 12 carbon atoms, more usually from 3 to about to 10 carbon atoms; still more usually from about 5 to about 8 carbon atoms. Non-limiting examples of cycloalkanes include cyclopentane, cyclohexane, cycloheptane, and cyclooctane. Cycloalkane can also be cyclodecane, cyclododecane or decaline. In a preferred embodiment, cycloalkane is cyclohexane.

Hydroperoxide Compound

Hydroperoxide compounds according to the present invention may be for example hydrogen hydroperoxide or an organic hydroperoxide.

Specific examples of the hydroperoxide compounds which are usable in the present invention may be represented by the formula (I) as follows:

$$R\text{—}O\text{—}O\text{—}H \qquad (I)$$

wherein R is a hydrocarbon group that may comprise from 1 to 15 carbon atoms, mainly alkyl or aryl groups.

As used herein, the term "hydrocarbon group" refers to a group consisting of carbon atoms and hydrogen atoms, which group may be saturated or unsaturated, linear, branched or cyclic, aliphatic or aromatic. Hydrocarbon groups of the present invention may be alkyl groups, alkenyl groups, or aryl groups.

Alkyl as used herein means a straight chain or branched saturated aliphatic hydrocarbon. As used herein, unless stated otherwise, the term "alkyl" means a linear or branched alkyl group optionally substituted with one or more substituent selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

Aryl as used herein means a 6-carbon monocyclic or 10-carbon bicyclic aromatic ring system wherein 0, 1, 2, 3, or 4 atoms of each ring are substituted by a substituent, such as O or N. Examples of aryl groups include phenyl, naphthyl and the like.

Hydroperoxides are preferably chosen in the group consisting of: tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin (i.e., tetrahydronaphtalene) hydroperoxide, isobutylbenzene hydroperoxide, and ethylnaphthalene hydroperoxide.

More preferably hydroperoxides are alkyl hydroperoxides such as tert-butyl hydroperoxide or cyclohexyl hydroperoxide.

These hydroperoxides may also be used in combination of two or more species thereof.

The hydroperoxide compound is advantageously used in a solution in an alkane. Any alkane can be used with a preference for cyclohexane. The concentration of the peroxide compound in the solution in an alkane, preferably in cyclohexane, is advantageous comprised between 0.1 wt % and 50 wt %, preferably between 2 wt % and 15 wt %.

In a preferred embodiment, no other oxidant agent than the hydroperoxide compound of the invention is used for the process of the invention. Advantageously no further oxidant agent such as pure oxygen, air, oxygen-enriched or oxygen-depleted air or, alternatively, oxygen diluted with an inert gas, is used for the process of the invention.

Cerium Oxide Based Catalyst

By "cerium oxide based catalyst" in the sense of the present invention, is understood:

Cerium oxide in the form of ceric oxide

A composition comprising cerium oxide and zirconium oxide

A composition comprising cerium oxide and at least one oxide of another rare earth A composition comprising cerium oxide and at least one compound of another rare earth A silicon-containing cerium composite oxide comprising silicon in terms of $SiO_2$ A cerium composite oxide comprising at least cerium oxide, silicon oxide and titanium oxide A cerium composite oxide comprising at least cerium oxide, silicon oxide, titanium oxide and at least one oxide of another rare earth, and/or A composition comprising cerium oxide, zirconium oxide and at least one oxide of another rare earth The cerium oxide of the invention is in the form of ceric oxide. Such a cerium oxide can for instance be produced according to a process as described in the documents EP 300852 or EP 388567. It can also be produced according to the document EP 1435338.

The cerium oxide of the invention may be in the form of ceric oxide nano-structures. Such nanostructures can for instance be produced according to a process described in the documents S. Laursen, D. Combita, M. Boronat, A. Corma, Angew. Chem. Int. Ed. 2012, 51, 4190-4193, or in H. Mai, L. Sun, Y. Zhang, R. Si, W. Feng, H. Zhang, H. Liu, C. Yan, J. Phys. Chem. B 2005, 109, 24380-24385).

Preferably, the "cerium oxide based catalyst" of the invention is cerium oxide in the form of ceric oxide.

The composition comprising cerium oxide and zirconium oxide can for instance be produced according to a process as described in the document US 2006/210462.

The expression "rare earth" is understood to mean the elements from the group made up of yttrium and the elements from the Periodic Table with atomic numbers between 57 and 71 inclusive.

In the remainder of the description, use will be made, for convenience, of the terms "rare earth" in the singular, but these terms should be understood, unless otherwise indicated, as applying both to the case where a single rare earth is present in the catalyst and to the case where several rare earths are also present.

The contents within the catalyst are given as the mass of oxides unless otherwise indicated, these oxides for the expression of these contents being considered in the form of ceric oxide for cerium, in the form Ln2O3 for the other lanthanides Ln and in the form Pr6O11 in the particular case of praseodymium.

According to a specific embodiment of the present invention, the "cerium oxide based catalyst" of the invention is a composition comprising cerium oxide and at least one oxide of another rare earth.

According to this embodiment, the other rare earth is preferably yttrium, neodymium, lanthanum, praseodymium or these last two elements in combination.

The content of rare-earth oxide is generally at most 25%, preferably when the rare earth is lanthanum, more particularly at most 20% and preferably at most 15% by weight. The minimum content is not critical but generally it is at least 1%. This content is expressed as oxide of the rare earth relative to the weight of the whole catalyst.

Such a catalyst can for instance be produced according to a process as described in the document US 2006/210462.

According to another embodiment of the present invention, the "cerium oxide based catalyst" of the invention is a composition comprising cerium oxide and at least one compound of another rare earth. In this case the cerium oxide is in the form of ceric oxide nano-structures as described above. The composition can be prepared according to a process described in the documents S. Laursen, D. Combita, M. Boronat, A. Corma, Angew. Chem. Int. Ed. 2012, 51, 4190-4193, or in H. Mai, L. Sun, Y. Zhang, R. Si, W. Feng, H. Zhang, H. Liu, C. Yan, J. Phys. Chem. B 2005, 109, 24380-24385), in which for instance $X(NO_3)_3 \cdot 6H_2O$ is added, X being a rare earth.

According to another embodiment of the present invention, the "cerium oxide based catalyst" of the invention is a silicon-containing cerium composite oxide comprising silicon in terms of $SiO_2$. For instance, this silicon-containing cerium composite oxide can comprise 2 to 20 mass % silicon in terms of $SiO_2$, preferably 5 to 20 mass % silicon in terms of $SiO_2$.

Such a catalyst can for instance be produced according to a process as described in the document US 2012/0316059.

According to another embodiment of the present invention, the "cerium oxide based catalyst" of the invention is a cerium composite oxide comprising at least cerium oxide, silicon oxide and titanium oxide, or a cerium composite oxide comprising at least cerium oxide, silicon oxide, titanium oxide and at least one oxide of another rare earth.

The cerium composite oxide can comprise at least:

silicon oxide in a proportion comprised between 1 and 15% by weight of oxide, preferably in a proportion comprised between 5 and 15% by weight of oxide; and titanium, oxide in a proportion comprised between 1 and 20% by weight of oxide, preferably in a proportion comprised between 5 and 15% by weight of oxide.

The cerium oxide is in the form of ceric oxide ($CeO_2$). Silicon oxide is $SiO_2$ and titanium oxide is $TiO_2$.

Cerium composite oxide may also comprise at least one rare earth element oxide, other than cerium oxide, notably in a proportion comprised between 1 and 15% by weight of oxide, preferably in a proportion comprised between 1 and 10% by weight of oxide. Several rare earth element oxides, other than, cerium oxide, may be used in the cerium composite oxide of the invention.

Preferably, rare earth element oxide are chosen in the group consisting of: lanthanium oxide ($La_2O_3$), praseodymium oxide ($Pr_6O_{11}$), neodymium oxide ($Nd_2O_3$) and yttrium oxide ($Y_2O_3$).

Preferably the cerium composite oxide comprises at least:
  cerium oxide, preferably in a proportion comprised between 60 and 95% by weight of oxide;
  silicon oxide in a proportion comprised between 1 and 15% by weight of oxide, preferably in a proportion comprised between 5 and 15% by weight of oxide;
  titanium oxide in a proportion comprised between 1 and 20% by weight of oxide, preferably in a proportion comprised between 5 and 15% by weight of oxide; and
  a rare earth element oxide, other than cerium oxide, in a proportion comprised between 1. and 15% by weight of oxide, preferably in a proportion comprised between 1 and 10% by weight of oxide.

Cerium oxide typically accounts for at least 50% by weight of the oxide. Preferably cerium oxide is at least 60% by weight. Cerium oxide typically does not exceed 98% by weight of the total weight of the oxide, preferably it does not exceed 95% by weight.

Such a catalyst can for instance be produced according to a process as described in the document WO 2014/202725.

According to another embodiment of the present invention, the "cerium oxide based catalyst" of the invention is a composition comprising cerium oxide, zirconium oxide and at least one oxide of another rare earth.

According to this embodiment, the other rare earth is preferably yttrium, neodymium, lanthanum, praseodymium or these last two elements in combination.

The content of rare-earth oxide, still expressed in oxide form, can be between 0.1 and 50% by weight, in particular between 0.1 and 45% by weight, more particularly between 0.1 and 20% by weight and preferably between 1 and 10% by weight, with respect to the whole catalyst.

Such a catalyst can for instance be produced according to a process as described in the document U.S. Pat. No. 6,214,306.

The contents within the catalyst are given as oxides unless otherwise indicated.

Catalyst of the present invention may be used in a range comprised between 0.0001 wt. % to 20 wt. %, preferably between 0.001 wt. % and 15 wt. %, more preferably between 0.01 and 10 wt. %, in relation to the total weight of the reaction medium.

A combination of two or more catalysts may be used during the reaction of the present invention, notably in blend.

Catalyst of the invention is used as such. It is not used as a carrier to support another catalyst, for instance a metal catalyst or a transition metal catalyst.

Catalyst of the invention does not contain metal catalyst or transition metal catalyst. On the other hand it may contain metal elements such as impurities which may especially originate from its preparation method, for example raw materials or starting reactants used.

Catalyst of the invention may be treated or not before its use in the process of the invention.

Different pretreatments can be undertaken with cerium oxide catalysts.

Cerium oxide catalyst can be calcined under air between 100° C. and 1000° C. in a static oven or under flowing air in a fixed bed reactor. The treatment can last 30 minutes to 10 h. The treatment can even last longer without modification of the properties of the material.

Alternatively, cerium oxide catalyst can be treated under pure $N_2$, pure $O_2$, a mixture of $O_2/N_2$, pure $H_2$, a mixture of $N_2/H_2$, $CO_2$ or a mixture of $H_2/CO_2$. The catalysts can be treated under flowing gas in a fixed bed reactor at temperatures varying between 100° C. and 1000° C. The treatment can last between 30 minutes and 10 h. The treatment can even last longer without modification of the properties of the material.

Parameters of the Reaction

In the practice of the invention, the catalysts can be contacted with a cycloalkane, such as cyclohexane, and a hydroperoxide in a fixed bed, which is arranged to provide intimate contact between the catalyst and reactants. Alternatively, catalysts can be slurried with reaction mixtures using techniques known in the art. The process of the invention is suitable for either batch or continuous cycloalkane oxidation. These processes can be performed under a wide variety of conditions, as will be apparent to persons of ordinary skill.

Suitable reaction temperatures for the process of the invention typically range from about 20 to about 200° C., advantageously from about 50 to about 180° C., preferably from about 70 to about 120° C., more preferably from about 80 to about 110° C.

The process according to the invention is performed advantageously at a pressure from 0.1 MPa (1 bar) to 2 MPa (20 bar), preferably from 0.1 MPa (1 bar) to 1 MPa (10 bar) and more preferably from 0.1 MPa (1 bar) to 0.3 MPa (3 bar).

Cycloalkane reactor residence time generally varies in inverse relation to reaction temperature, and typically is comprised between 30 and 1440 minutes.

The catalysts of the present invention may be recovered, and regenerated by a conventionally known method. More specifically, the catalyst may be regenerated so that it recovers an initial activity, for example, by recovering and drying the catalyst, or by calcining the catalyst in air.

At the end of the reaction, the compound of interest may be eventually purified by well known methods of the technical field, such as distillation.

Should the disclosure of any of the patents, patent applications, and publications which are incorporated herein by reference conflict with the description of the present application to the extent that it may render a term unclear, the present description shall take precedence.

The following examples are provided for illustrative purposes only and should not be regarded as limiting the invention.

EXPERIMENTAL PART

Abbreviations $^t$BuOOH: tert-butyl hydroperoxide
CyOH: cyclohexanol
CyO: cyclohexanone
CyOOH: cyclohexyl hydroperoxide Definition of Terms Conversion is defined as the ratio between the number of moles of hydroperoxide ROOH consumed divided by the number of initial moles of ROOH.

$$\text{Conversion}(\%) = 100 \times \frac{n\text{ROOH(consumed)}}{n\text{ROOH(initial)}}$$

In the case of tBuOOH decomposition, selectivity is defined as the number of moles of Cyclohexanol (CyOH) and cyclohexanone (CyO) produced divided by the number of moles of tBuOOH consumed.

$$\text{Selectivity}(\%) = 100 \times \frac{n\,\text{CyO (produced)} + n\,\text{CyOH (produced)}}{n\,\text{tBuOOH(consumed)}}$$

If selectivity is 0, catalyst decomposes tBuOOH without oxidizing cyclohexane. If selectivity is higher than 0, catalyst is able to decompose the peroxide and oxidize cyclohexane at the same time In the case of CyOOH decomposition, selectivity is defined as the number of moles of Cyclohexanol (CyOH) and cyclohexanone (CyO) produced divided by the number of moles of CyOOH consumed.

$$\text{Selectivity}(\%) = 100 \times \frac{n\,\text{CyO (produced)} + n\,\text{CyOH (produced)}}{n\,\text{CyOOH(consumed)}}$$

When selectivity is lower or equal to 100%, catalyst only decomposes CyOOH without oxidizing cyclohexane.

When selectivity is higher than 100%, catalyst is able to decompose the peroxide and oxidize cyclohexane at the same time.

Analysis

Iodometry

Cyclohexyl hydroperoxide (CyOOH) is quantified by iodometry which consists in reacting CyOOH with KI to yield cyclohexanol and $I_2$. The amount of $I_2$ formed is estimated by potentiometry by reaction of $I_2$ with $Na_2S_2O_3$.

About 1 g of the solution containing CyOOH is weighed in an Erlenmeyer flask. Then, 20 mL of 80% acetic acid, about 1 g of sodium hydrogenocarbonate ($NaHCO_3$) and about 1 g of potassium iodide (KI) are introduced. $NaHCO_3$ is a weak base and reacts with acetic acid to produce $CO_2$, so that $O_2$ is pushed away. Indeed, the presence of $O_2$ would induce error on the evaluation of CyOOH quantity.

After mixing, the Erlenmeyer flask is stored 20 minutes in the dark. The Erlenmeyer flask is washed with distilled water and acetonitrile (which avoid the formation of foam). The solution is dosed with a solution of sodium thiosulfate $Na_2S_2O_3$ (0.1 N). The same method is used to quantify tert-butyl hydroperoxide (tBuOOH).

GC (gas chromatography)

GC Used to Quantify Cyclohexanol and Cyclohexanone Formed after tBuOOH Decomposition The reaction mixture contains cyclohexane, tert-butyl hydroperoxide, cyclohexanol, cyclohexanone, tert-butanol and small amounts of other byproducts, like carboxylic acids or diols.

Tert-butyl hydroperoxide is quantified by iodometry, while cyclohexanol and cyclohexanone formed during the reaction are quantified by GC using a Varian CP-3800 chromatograph with a HP-5 column (0.25 μm film thickness, length 25 m, inner diameter 0.25 mm). For each sample, 30 μL are extracted from the glass reactor vessel using a syringe and introduced in a vial containing cyclohexane. The amount of tBuOOH is measured by iodometry.

GC Used to Quantify Cyclohexanol, Cyclohexanone and CyOOH after CyOOH Decomposition The reaction mixture contains cyclohexane, cyclohexyl hydroperoxide, cyclohexanol, cyclohexanone, and small amounts of other byproducts (carboxylic acids, diols, lactones, peroxide) which are quantified by GC using a specific polar column (Permabond FFAP 0.10 μm film thickness, length 20 m). The amount of CyOOH of calibration solution is measured by iodometry.

Dinitrogen physisorption for BET area quantification was performed on a Micromeritics ASAP®2420 Accelerated Surface Area and Porosimetry System at 77 K. BET analyses allowed to determine the surface area of the catalysts.

Materials:

Cyclohexyl Hydroperoxide (CyOOH) Solution in Cyclohexane

CyOOH was extracted from a cyclohexane oxidate resulting from the thermal oxidation of cyclohexane by oxygen in an industrial unit. The oxidate was washed with water first then it was extracted with 1 M NaOH. The water phase was then extracted with ether and was neutralized with a chilled aqueous 4 M HCl. solution until slightly acidic. The water phase was subsequently extracted 3 times with cyclohexane and dried over $Na_2SO_4$ or $MgSO_4$. The solution was concentrated to reach a concentration of 4.7 wt % or 5.6 wt % CyOOH.

Tert-Butyl Hydroperoxide (tBuOOH) Solution in Cyclohexane

The reaction mixture is prepared from a commercial solution of $^t$BuOOH diluted in water (3:2 $^t$BuOOH: water, ie 80% in mass percentage) from Fluka, and cyclohexane (>99% purity). The proper amount of $^t$BuOOH solution and cyclohexane is mixed. Molecular sieves are added to the solution in order to absorb the water and make the mixture anhydrous. The exact amount of $^t$BuOOH in the final mixture is analyzed by iodometry. The mixture is then stored in darkness at low temperature (10° C.) until it is used for reaction.

$CeO_2$ Based Catalyst from the Invention $CeO_2$: this catalyst can be produced according to a process described in EP 300852 or EP 388567

$CeO_2$ Aldrich: cerium oxide commercialized by Aldrich.

$CeO_2$ nano-structures (rods, octahedral, cubes): these catalysts can be produced according to a process described in references [1] or [2] ([1] S. Laursen, D. Combita, M. Boronat, A. Corma, *Angew. Chem. Int. Ed.* 2012, 51, 4190-4193 and [2] H. Mai, L. Sun, Y. Zhang, R. Si, W. Feng, H. Zhang, H. Liu, C. Yan, *J. Phys. Chem. B* 2005, 109, 24380-24385). A solution of NaOH was added under vigorous stirring to a solution of $Ce(NO_3)_3.6H_2O$ (Aldrich, Analytical grade). The formed suspension was kept stirring for 30 minutes. This step produces seeds for the hydrothermal growth. This milky slurry was transferred to a Teflon liner autoclave and the autoclave was sealed tightly. The autoclave was transferred to an oven for the hydrothermal treatment during 24 hours. Table 1 shows the conditions for each type of $CeO_2$ nano-structure. After cooling down at room temperature, the precipitated yellow-white solids were filtered and washed thoroughly with distillated water, controlling the pH of the filtrates. After that, the samples were dried at 120° C., under flowing air for 12 hours.

TABLE 1

Synthesis parameters for the production of the CeO$_2$ nano-structures.

| SHAPE | V$_{Sol.\ NaOH}$/V$_{Sol.\ Ce+3}$ | [NaOH] (M) | [Ce$^{+3}$] (M) | T (° C.) |
|---|---|---|---|---|
| Cubes | 7 | 9 | 5 | 200 |
| Octahedra | 7 | 1 | 5 | 175 |
| Rods | 7 | 9 | 5 | 100 |

Doped CeO$_2$ nano-rods: The procedure is essentially the same as described above for CeO$_2$ nano-structures, with an additional step in which the proper amount of X(NO$_3$)$_3$.6H$_2$O (Sigma-Aldrich, Analytical grade, X=La,Pr,Y, CAS: 10277-43-7, 15878-77-0, 13773-69-8 respectively) is added to the Ce(NO$_3$)$_3$.6H$_2$O solution before addition of NaOH. The content of X in the catalyst is 1 wt %.

Ce—Zr: mixture of CeO$_2$ and ZrO$_2$
Ce—Zr—La: mixture of CeO$_2$, ZrO$_2$ and La$_2$O$_3$
Ce—Zr—Pr: mixture of CeO$_2$, ZrO$_2$ and Pr$_6$O$_{11}$
Ce—La—Pr: mixture of CeO$_2$, La$_2$O$_3$ and Pr$_6$O$_{11}$
Ce—Pr: mixture of CeO$_2$ and Pr$_6$O$_{11}$
Ce—Si: mixture of CeO$_2$ and SiO$_2$
Ce—Si—Ti: mixture of CeO$_2$, SiO$_2$ and TiO$_2$
Ce—Si—Ti—La: mixture of CeO$_2$, SiO$_2$, TiO$_2$ and La$_2$O$_3$ The numbers mentioned in the "composition" columns of the tables below correspond to the weight percentage of the different oxides (CeO$_2$, ZrO$_2$, La$_2$O$_3$ and/or Pr$_6$O$_{11}$) present in the catalysts.

Some of these catalysts are commercial products from Solvay.

Other Catalysts (for Comparison)
Titanium dioxide (TiO$_2$): commercial product from Aldrich
Zirconium dioxide (ZrO$_2$): commercial product from Aldrich
Molybdenum oxide (MoO$_2$): commercial product from Aldrich
Praseodymium oxide (Pr$_6$O$_{ii}$): commercial product from Aldrich
Calcium oxide (CaO): commercial product from Aldrich
Gallium oxide (Ga$_2$O$_3$): commercial product from Aldrich
Germanium oxide (GeO$_2$): commercial product from Aldrich
Yttrium oxide (Y$_2$O$_3$): commercial product from Aldrich
Tin oxide (SnO and SnO$_2$): commercial products from Aldrich
Hafnium oxide (HfO$_2$): commercial product from Aldrich
Tantalum oxide (Ta$_2$O$_5$): commercial product from Aldrich
Neodymium oxide (Nd$_2$O$_3$): commercial product from Aldrich
Samarium oxide (Sm$_2$O$_3$): commercial product from Aldrich
Europium oxide (Eu$_2$O$_3$): commercial product from Aldrich
Erbium oxide (Er$_2$O$_3$): commercial product from Aldrich
Zinc oxide (ZnO): commercial product from Fluka
Tungsten oxide (W$_2$O$_3$); commercial product from Fluka
High surface area titanium dioxide (TiO$_2$ HSA): commercial product from Mirkat
Magnesium oxide (MgO 600 m$^2$/g): commercial product from Nanoactive
Alumina (Al$_2$O$_3$ 550 m$^2$/g): commercial product from Nanoactive
Niobium oxide (Nb$_2$O$_5$): commercial product from Alfa Aesar
Lanthanum oxide (La$_2$O$_3$): commercial product from Merck Catalyst Pre-Treatment.

Calcination:

Catalysts can be calcined before reaction under the following classical conditions. The catalyst is placed into a porcelain evaporating dish, it is introduced in the oven and calcined in static air with the following temperature program: 4 hours gradient from room temperature to 400° C., and then an isotherm of 400° C. for 4 hours. The catalyst is kept inside the oven until the reaction is to be performed.

Gas Flow.

The catalyst can also be treated under different gas flow. The catalyst is placed into the batch reactor, and a stirrer is also introduced in the system. Then, a flow of the desired gas for the treatment (N$_2$, H$_2$, or O$_2$) is introduced through the vent valve, and the flow is controlled with a flowmeter (15-20 mL/min). While the gas is passing through the system, stirring is active to ensure that the gas reaches all catalyst mass. Temperature is kept constant at the desired value (135° C. or 85° C. for N$_2$ and 85° C. for H$_2$ and O$_2$) during the treatment that takes 45 min.

General Conditions of tBuOOH Deperoxidation Reaction:

Reactor.

The reaction is performed in a batch reactor consisting of:
a glass reactor vessel (chemical and thermal shock resistant, 2 mL Volume capacity, Duran Manufacturer).
a vent valve (Gas inlet, for pressurizing/depressurizing the system with nitrogen).
an outlet micro valve for sample taking.
a pressure gauge (Pressure range: 1-16 bar).
a magnetic stirring bar, which is stored inside the reaction media in the reactor vessel.

To ensure that the reactor is completely clean and no traces of contaminants are present, it is first washed with acetone, then with cyclohexane, and after that dry air is passed through.

Reaction Procedure.

The proper amount (16 mg) of catalyst is introduced in the reactor. Then, 200 μL of internal standard Undecane (99% purity, from Sigma-Aldrich) are introduced in the glass reactor vessel and its exact mass weighted.

Next, the reactor is opened, 2 mL of the tert-butyl hydroperoxide/cyclohexane solution is introduced, and its exact mass weighted. Finally, a magnetic stir bar is introduced and the reactor is closed. An overpressure of nitrogen is then added in order to increase the boiling point of cyclohexane and keep reaction media at liquid state. The gas is introduced through the vent valve until an internal pressure in the reactor within 4 to 6 atmosphere is reached.

An aluminium container for reactors, at the desired reaction temperature (100° C.), is kept on a hot-stirring plate. The stirring is set to 1400 rpm. The glass reactor vessel is introduced in the container, and the reaction starts.

To follow the reaction progress, samples are taken at different times and their composition analyzed by iodometry (t-butyl hydroperoxide) and Gas Chromatography (cyclohexanol and cyclohexanone). At each time, the reactor is first taken off the container and stored in a water bath at room temperature, in order to cool down the reaction media. Once the reactor is at room temperature, three different samples are taken from it through the outlet micro valve and analyzed.

Examples 1 to 20 (According to the Invention)

It is observed that pretreatment has an influence on activity and selectivity of CeO$_2$. The CeO$_2$ catalyst has been treated under different gas flows as described in the "catalyst pre-treatment" section above or calcined at 500° C. according to the following procedure: The CeO$_2$ catalyst (16 mg) is placed into a porcelain evaporating dish, it is introduced in the oven and calcined in static air with the following temperature program: 3 hours gradient from room temperature to 500°, and then an isotherm of 500° for 5 hours. The catalyst is kept inside the oven until the reaction is to be performed.

The CeO$_2$ Aldrich catalyst (16 mg) is calcined under classical conditions before test as described in the "catalyst pre-treatment" section above.

The catalyst was tested under the conditions specified above (see "reaction procedure" section above) at 100° C.

In all cases, selectivity is positive, meaning CeO$_2$ is able to oxidize cyclohexane in the presence of tBuOOH.

The catalyst of example 20 has a surface area of 12.7 m$^2$/g.

The catalyst of examples 21 to 23 has a surface area of 159.8 m$^2$/g, and the catalyst of examples 24 to 26 has a surface area of 115.9 m$^2$/g.

TABLE 3

Catalytic performance of CeO$_2$ calcined between 600° C. and 800° C. after test in 7.37 wt % tBuOOH/cyclohexane solution at 100° C.

| Example | Catalyst | t(h) | Conversion % | Selectivity (%) |
|---|---|---|---|---|
| 21 | CeO$_2$ calcined at 600° C. | 3 | 58 | 34 |
| 22 | CeO$_2$ calcined at 600° C. | 6 | 77 | 33 |
| 23 | CeO$_2$ calcined at 600° C. | 9 | 81 | 29 |
| 24 | CeO$_2$ calcined at 700° C. | 3 | 48 | 40 |
| 25 | CeO$_2$ calcined at 700° C. | 6 | 67 | 33 |

TABLE 2

Catalytic performance of CeO$_2$ after test in tBuOOH/cylohexane solution

| Example | Wt % tBuOOH | Catalyst | Catalyst Pre-treatment | Reaction T (° C.) | t (h) | Conversion % | Selectivity % |
|---|---|---|---|---|---|---|---|
| 1 | 11.9 | CeO$_2$ | — | 80 | 8 | 43 | 53 |
| 2 | 11.9 | CeO$_2$ | N$_2$ at 135° C. | 80 | 8 | 49 | 35 |
| 3 | 11.9 | CeO$_2$ | N$_2$ at 135° C. | 80 | 11 | 57 | 34 |
| 4 | 11.9 | CeO$_2$ | N$_2$ at 85° C. | 80 | 8 | 41 | 29 |
| 5 | 11.9 | CeO$_2$ | N$_2$:O$_2$ 95:5 in volume at 85° C. | 80 | 8 | 38 | 34 |
| 6 | 11.9 | CeO$_2$ | O$_2$ at 85° C. | 80 | 8 | 44 | 40 |
| 7 | 11.9 | CeO$_2$ | H$_2$ at 85° C. | 80 | 8 | 28 | 26 |
| 8 | 11.9 | CeO$_2$ | calcined at 500° C. | 80 | 8 | 33 | 60 |
| 9 | 11.3 | CeO$_2$ | N$_2$ at 85° C. | 85 | 4 | 33 | 39 |
| 10 | 11.3 | CeO$_2$ | N$_2$ at 85° C. | 85 | 8 | 46 | 39 |
| 11 | 11.3 | CeO$_2$ | N$_2$ at 85° C.c | 100 | 4 | 39 | 61 |
| 12 | 11.3 | CeO$_2$ | N$_2$ at 85° C. | 100 | 8 | 73 | 36 |
| 13 | 11.3 | CeO$_2$ | N$_2$ at 85° C. | 120 | 4 | 48 | 54 |
| 14 | 11.3 | CeO$_2$ | N$_2$ at 85° C. | 120 | 8 | 83 | 31 |
| 15 | 11.3 | CeO$_2$ | calcined at 500° C. | 85 | 4 | 24 | 48 |
| 17 | 11.3 | CeO$_2$ | calcined at 500° C. | 85 | 8 | 34 | 60 |
| 18 | 11.3 | CeO$_2$ | calcined at 500° C. | 100 | 4 | 44 | 43 |
| 19 | 11.3 | CeO$_2$ | calcined at 500° C. | 100 | 8 | 74 | 34 |
| 20 | 6.0 | CeO$_2$ Aldrich | calcined at 400° C. | 100 | 9 | 33 | 21 |

Examples 21 to 29 (According to the Invention)

CeO$_2$ was calcined at 600° C., 700° C. and 900° C. according to the following procedure: They were placed into a porcelain evaporating dish, introduced in the oven and calcined in static air with the following temperature program: from room temperature to final temperature at 0.5° C./min, and then an isotherm at the desired temperature for 4 hours.

They were tested under the conditions specified above (see "reaction procedure" section above) at 100° C. in a 7.37 wt % tBuOOH/cyclohexane solution. It is observed that selectivity is positive in all cases meaning that these catalysts are able to oxidize cyclohexane. However, increasing calcination temperature resulted in the decrease of activity and selectivity.

TABLE 3-continued

Catalytic performance of CeO$_2$ calcined between 600° C. and 800° C. after test in 7.37 wt % tBuOOH/cyclohexane solution at 100° C.

| Example | Catalyst | t(h) | Conversion % | Selectivity (%) |
|---|---|---|---|---|
| 26 | CeO$_2$ calcined at 700° C. | 9 | 78 | 29 |
| 27 | CeO$_2$ calcined at 900° C. | 3 | 18 | 29 |
| 28 | CeO$_2$ calcined at 900° C. | 6 | 36 | 27 |
| 29 | CeO$_2$ calcined at 900° C. | 9 | 42 | 27 |

Examples 30 to 37 (According to the Invention)

CeO$_2$ doped with La and/or Pr, ZrO$_2$—CeO$_2$ mixed oxides and CeO$_2$—ZrO$_2$ mixed oxides doped with La or Pr were calcined under classical conditions before test as described in the "catalyst pre-treatment" section.

They were tested under the conditions specified above at 100° C. in a 7.57 wt % tBuOOH/cyclohexane solution. Selectivity is positive in each cases meaning all catalysts are able to oxidize cyclohexane.

The catalyst of example 30 has a surface area of 221.9 m$^2$/g.

TABLE 4

Catalytic performance of CeO$_2$ doped with La and/or Pr, ZrO$_2$—CeO$_2$ mixed oxides and CeO$_2$—ZrO$_2$ mixed oxides doped with La or Pr after 9 h in 7.57 wt % tBuOOH/cyclohexane solution at 100° C. (see "reaction procedure" section above)

| Example | Catalyst | Composition | Conversion (%) | Selectivity (%) |
|---|---|---|---|---|
| 30 | CeO$_2$ | (100) | 88 | 34 |
| 31 | Ce—Pr | (90-10) | 86 | 36 |
| 32 | Ce—Zr—Pr | (90-5-5) | 85 | 31 |
| 33 | Ce—La—Pr | (90-5-5) | 76 | 34 |
| 34 | Ce—Zr—La | (86-10-4) | 59 | 35 |
| 35 | Ce—Zr—La | (20-75-5) | 47 | 26 |
| 36 | Ce—Zr | (70-30) | 69 | 37 |
| 37 | Ce—Zr | (57-43) | 64 | 37 |

Examples 38 to 40 (According to the Invention)

CeO$_2$—SiO$_2$ mixed oxides, CeO$_2$—SiO$_2$—TiO$_2$ mixed oxides or CeO$_2$—SiO$_2$—TiO$_2$ mixed oxides doped with La, were calcined under classical conditions before test as described in the "catalyst pre-treatment" section.

They were tested under the conditions specified above at 100° C. in a 7.85 wt % tBuOOH/cyclohexane solution. Selectivity is positive in each cases meaning all catalysts are able to oxidize cyclohexane.

TABLE 5

Catalytic performance of CeO$_2$ mixed oxides alone or doped with La after 9 h in 7.85 wt % tBuOOH/cyclohexane solution at 100° C. (see "reaction procedure" section above)

| Example | Catalyst | Composition | Conversion (%) | Selectivity (%) |
|---|---|---|---|---|
| 38 | Ce—Si | (98-2) | 91 | 24 |
| 39 | Ce—Si—Ti | (90-5-5) | 99 | 26 |
| 40 | Ce—Si—Ti—La | (80-10-5-5) | 99 | 25 |

Examples 41 to 43 (According to the Invention)

CeO$_2$ nanostructures were calcined under classical conditions before test as described in the "catalyst pre-treatment" section.

They were tested under the conditions specified above at 100° C. in a 7.57 wt % tBuOOH/cyclohexane solution. Selectivity is positive in each cases meaning all catalysts are able to oxidize cyclohexane. Cubes were found less active and selective than octahedra, and the best performance was obtained for rods.

TABLE 6

Catalytic performance of nanostructures of CeO$_2$ after 9 h in 7.57 wt % tBuOOH/cyclohexane solution at 100° C. (see "reaction procedure" section above)

| Example | Morphology | Surface area (m$^2$/g) | Conversion (%) | Selectivity (%) |
|---|---|---|---|---|
| 41 | Rods | 111.0 | 86 | 29 |
| 42 | Octahedra | 64.9 | 67 | 26 |
| 43 | Cubes | 31.2 | 31 | 25 |

Examples 44 to 67 (Comparative Examples)

Different oxides were calcined before test under classical conditions as described in "catalyst pretreatment" section above. In some cases, they were treated under N$_2$. They were tested in tBuOOH/cyclohexane solution at 80° C. and 100° C. (see "reaction procedure" section above). Results are presented in Table 7.

TiO$_2$ and Sm$_2$O$_3$ oxides are inactive.

CaO, MgO, ZnO, TiO$_2$ HSA, La$_2$O$_3$, Ga$_2$O$_3$, GeO$_2$, Y$_2$O$_3$, Nb$_2$O$_5$, SnO, SnO$_2$, HfO$_2$, Ta$_2$O$_5$, Nd$_2$O$_3$, Eu$_2$O$_3$ and Er$_2$O$_3$ oxides are weakly active with a conversion lower than 24% but able to oxidize cyclohexane.

Pr$_6$O$_{11}$, W$_2$O$_3$ and ZrO$_2$ decompose tBuOOH with a low conversion and do not oxidize cyclohexane.

MoO$_2$ oxide is active with a high conversion but selectivity is low (17%). Catalyst of the invention represents the best compromise with a high activity (conversion 88%) and the highest selectivity obtained (34%). Hence, catalyst of the invention is the best oxide to decompose tBuOOH and oxidize cyclohexane.

TABLE 7

Catalytic performance of oxides after 9 h in tBuOOH/cyclohexane

| Example | Catalyst | Wt % tBuOOH | T° C. | Catalyst pre-treatment | Conversion % | Selectivity % |
|---|---|---|---|---|---|---|
| 44 | CaO | 7 | 100 | Calcined | 11 | 14 |
| 45 | TiO$_2$ | 5 | 80 | N$_2$ at 135° C. | <5% | 0 |
| 46 | ZrO$_2$ | 5 | 80 | N$_2$ at 135° C. | <5% | 0 |
| 47 | ZrO$_2$ | 7 | 100 | Calcined | 12 | 2 |
| 48 | MgO | 7 | 100 | Calcined | 10.8 | 28 |
| 49 | ZnO | 7 | 100 | Calcined | 10 | 25 |
| 50 | W$_2$O$_3$ | 7 | 100 | Calcined | 8 | 0 |
| 51 | TiO$_2$ HSA | 7 | 100 | Calcined | 18 | 25 |

TABLE 7-continued

Catalytic performance of oxides after 9 h in tBuOOH/cyclohexane

| Example | Catalyst | Wt % tBuOOH | T° C. | Catalyst pre-treatment | Conversion % | Selectivity % |
|---|---|---|---|---|---|---|
| 52 | $MoO_2$ | 7 | 100 | — | 70 | 15 |
| 53 | $MoO_2$ | 7 | 100 | Calcined | 98.5 | 17 |
| 54 | $La_2O_3$ | 7 | 100 | Calcined | 16.6 | 27 |
| 55 | $Pr_6O_{11}$ | 7 | 100 | Calcined | 11 | 0 |
| 56 | $Ga_2O_3$ | 7 | 100 | Calcined | 12 | 18 |
| 57 | $GeO_2$ | 7 | 100 | Calcined | 10 | 14 |
| 58 | $Y_2O_3$ | 7 | 100 | Calcined | 13 | 16 |
| 59 | $Nb_2O_5$ | 7 | 100 | Calcined | 22 | 15 |
| 60 | SnO | 7 | 100 | Calcined | 15 | 17 |
| 61 | $SnO_2$ | 7 | 100 | Calcined | 14 | 15 |
| 62 | $HfO_2$ | 7 | 100 | Calcined | 7 | 19 |
| 63 | $Ta_2O_5$ | 7 | 100 | Calcined | 9 | 12 |
| 64 | $Nd_2O_3$ | 7 | 100 | Calcined | 12 | 20 |
| 65 | $Sm_2O_3$ | 7 | 100 | Calcined | 0 | 0 |
| 66 | $Eu_2O_3$ | 7 | 100 | Calcined | 23 | 14 |
| 67 | $Er_2O_3$ | 7 | 100 | Calcined | 16 | 17 |

General Conditions of CyOOH Deperoxidation Reaction:
Reactor

The reaction is performed in a Teflon batch reactor consisting of:
- a teflon reactor vessel (40 mL Volume capacity, Bola Manufacturer)
- an outlet micro valve for sample taking.
- a pressure gauge.
- a thermocouple
- a magnetic stirring bar, which is stored inside the reaction media in the reactor vessel.

To ensure that the reactor is completely clean and no traces of contaminants are present, it is first washed with acetone, then with water. In case some trace of metal remains on the reactor wall, it is washed with diluted HCl.

Reaction Procedure

The proper amount (160 mg) of catalyst is introduced in the reactor. Then, 0.6 g of internal standard orthodichlorobenzene (99% purity, from Sigma-Aldrich) are introduced in the teflon reactor.

Next, the reactor is opened, about 16 g of the CyOOH purified solution are introduced and its exact mass weighted. Finally, a magnetic stir bar is introduced and the reactor is closed.

A silicon bath at the desired reaction temperature (typically 100° C.) is kept on a hot-stirring plate. The glass reactor vessel is introduced in the silicon bath. It takes about 30 minutes to reach 100° C. inside the reactor. During this transition period of heat, the stirring is off to slow down reaction between room temperature and 100° C.

The follow up of reaction and stirring of the mixture begin when temperature reaches 100° C. To follow the reaction progress, samples are taken at different times and their composition analyzed by Gas Chromatography. The medium is sampled through a syringe and put in a GC vial when it is cold.

Examples 68 to 69 (According to the Invention)

The $CeO_2$ catalyst is calcined in a static air oven at 500° C. prior to reaction. The $CeO_2$ catalyst (160 mg) is placed into a porcelain evaporating dish, it is introduced in the oven and calcined in static air at 500° C. during 13 h. Reaction is performed as described above. Selectivities higher than 100% are obtained meaning $CeO_2$ is able to oxidize cyclohexane in the presence of CyOOH (Table 8).

TABLE 8

Catalytic performance of $CeO_2$ after test in 4.7 wt % CyOOH/cyclohexane solution at 100° C.

| Example | t(h) | Conversion % | Selectivity % |
|---|---|---|---|
| 68 | 5 h 30 | 92.8 | 113 |
| 69 | 21 h 30 | 99.8 | 113 |

Examples 70 to 76 (According to the Invention)

$CeO_2$ doped with La and/or Pr, $ZrO_2$—$CeO_2$ mixed oxides and $CeO_2$—$ZrO_2$ mixed oxides doped with La or Pr were used without calcination. Results are presented in Table 9. It can be observed that selectivities higher than 100% are obtained, meaning these catalysts are able to oxidize cyclohexane.

TABLE 9

Catalytic performance of doped $CeO_2$ and mixed oxides after test in 4.7 wt % CyOOH/cyclohexane solution at 100° C. (see "reaction procedure" section above)

| Example | Catalyst | Composition | T(h) | Conversion % | Selectivity % |
|---|---|---|---|---|---|
| 70 | Ce—Zr | 70-30 | 5 h 30 | 97 | 108 |
| 71 | Ce—Zr | 57-43 | 5 h 30 | 88 | 108 |
| 72 | Ce—Zr—La | 86-10-4 | 5 h 30 | 95 | 113 |
| 73 | Ce—Zr—La | 20-75-5 | 6 h | 41 | 107 |
| 74 | Ce—Zr—Pr | 90-5-5 | 6 h | 100 | 107 |
| 75 | Ce—La—Pr | 90-5-5 | 5 h 30 | 99 | 104 |
| 76 | Ce—Pr | 90-10 | 5 h 50 | 100 | 106 |

Examples 77 to 85 (According to the Invention)

$CeO_2$—$SiO_2$ mixed oxides, $CeO_2$—$SiO_2$—$TiO_2$ mixed oxides or $CeO_2$—$SiO_2$—$TiO_2$ mixed oxides doped with La, were used without calcination. Results are presented in Table 10. It can be observed that selectivities higher than 100% are obtained, meaning these catalysts are able to oxidize cyclohexane.

TABLE 10

Catalytic performance of $CeO_2$ mixed oxides alone or doped with La after test in 4.9 wt % CyOOH/cyclohexane solution at 100° C. (see "reaction procedure" section above)

| Example | Catalyst | Composition | Time | Conversion (%) | Selectivity (%) |
|---|---|---|---|---|---|
| 77 | Ce—Si | (95-5) | 2 h | 93 | 104 |
| 78 | Ce—Si | (95-5) | 4 h | 99 | 104 |
| 79 | Ce—Si | (98-2) | 1 h 45 | 60 | 104 |
| 80 | Ce—Si | (98-2) | 4 h 30 | 93 | 104 |
| 81 | Ce—Si | (98-2) | 5 h 45 | 98 | 102 |
| 82 | Ce—Si—Ti | (90-5-5) | 2 h | 92 | 106 |
| 83 | Ce—Si—Ti | (90-5-5) | 4 h | 99 | 105 |
| 84 | Ce—Si—Ti—La | (80-10-5-5) | 2 h | 62 | 108 |
| 85 | Ce—Si—Ti—La | (80-10-5-5) | 4 h | 99 | 108 |

Examples 86 to 102 (According to the Invention)

$CeO_2$ nanostructures with rod, cube or oroctahedra morphology were tested as such or after doping with La, Pr, or Y. Selectivity is higher than 100% in each cases meaning all catalysts are able to oxidize cyclohexane.

TABLE 11

Catalytic performance of $CeO_2$ nanostructures and $CeO_2$ rods doped with La, Pr, or Y after test in 5.0 wt % CyOOH/cyclohexane solution at 100° C. (see "reaction procedure" section above)

| Example | Catalyst | t(h) | Conversion % | Selectivity (%) |
|---|---|---|---|---|
| 86 | $CeO_2$ rods | 3 | 97 | 107 |
| 87 | $CeO_2$ rods | 6 | 100 | 104 |
| 88 | $CeO_2$ rods | 9 | 100 | 104 |
| 89 | $CeO_2$ cubes | 3 | 26 | 105 |
| 90 | $CeO_2$ cubes | 6 | 44 | 115 |
| 91 | $CeO_2$ cubes | 9 | 58 | 111 |
| 92 | $CeO_2$ octahedra | 3 | 22 | 127 |
| 93 | $CeO_2$ octahedra | 6 | 51 | 113 |
| 94 | $CeO_2$ octahedra | 9 | 75 | 104 |
| 95 | $CeO_2$ rods La-doped | 6 | 100 | 104 |
| 96 | $CeO_2$ rods La-doped | 9 | 100 | 101 |
| 97 | $CeO_2$ rods Pr-doped | 3 | 92 | 107 |
| 98 | $CeO_2$ rods Pr-doped | 6 | 99 | 108 |
| 99 | $CeO_2$ rods Pr-doped | 9 | 100 | 110 |
| 100 | $CeO_2$ rods Y-doped | 3 | 80 | 109 |
| 101 | $CeO_2$ rods Y-doped | 6 | 96 | 107 |
| 102 | $CeO_2$ rods Y-doped | 9 | 100 | 108 |

Examples 103 to 104 (Comparative Examples)

$Al_2O_3$ and MgO were calcined under classical conditions (see "catalyst pre-treatment section" above) before reaction with 5.6 wt % CyOOH/cyclohexane solution. 16 mg of catalyst and 2 mL of CyOOH/cyclohexane solution were placed in the reactor and heated to 100° C. (see "reaction procedure" section above). Results are presented in Table 12. After 6 hours, no reaction took place, so these oxides are not active to decompose CyOOH.

TABLE 12

Catalytic performance of different oxides after test in 5.6% CyOOH/cyclohexane solution at 100° C.

| Example | Catalyst | Treatment | t (h) | Conversion (%) | Selectivity (%) |
|---|---|---|---|---|---|
| 103 | $Al_2O_3$ | Calcined. at 500° C. | 8 | <5% | 0 |
| 104 | MgO | Calcined at 500° C. | 8 | <5% | 0 |

Example 105 (Comparative Example)

Reactor

The reaction is performed in a Teflon batch reactor consisting of:
 a teflon reactor vessel (40 mL Volume capacity, Bola Manufacturer)
 an outlet micro valve for sample taking.
 a pressure gauge.
 a thermocouple
 a magnetic stirring bar, which is stored inside the reaction media in the reactor vessel.

To ensure that the reactor is completely clean and no traces of contaminants are present, it is first washed with acetone, then with water. In case some trace of metal remains on the reactor wall, it is washed with diluted HCl.

Reaction Procedure

The proper amount (160 mg) of $CeO_2$ (without pretreatment) is introduced in the reactor. Then, 0.6 g of internal standard undecane (99% purity, from Sigma-Aldrich) are introduced in the teflon reactor.

Next, the reactor is opened, about 16 g of cyclohexane (99.8% purity, from Sigma-Aldrich) are introduced and its exact mass weighted. Finally, a magnetic stir bar is introduced and the reactor is closed. The reactor is kept in an air atmosphere. No nitrogen overpressure is added.

A silicon bath at the desired reaction temperature (typically 100° C.) is kept on a hot-stirring plate. The glass reactor vessel is introduced in the silicon bath. It takes about 30 minutes to reach 100° C. inside the reactor. During this transition period of heat, the stirring is off to slow down reaction between room temperature and 100° C.

The follow up of reaction and stirring of the mixture begin when temperature reaches 100° C. To follow the reaction progress, samples are taken at different times and their composition analyzed by Gas Chromatography. The medium is sampled through a syringe and put in a GC vial when it is cold.

No conversion of cyclohexane was obtained after 24 hours.

So $CeO_2$ is not able to oxidize cyclohexane with air.

The invention claimed is:

1. A method of oxidizing a cycloalkane to form a product mixture containing a corresponding alcohol and ketone, said method comprising contacting a cycloalkane with a cyclohexyl hydroperoxide compound in the presence of at least a cerium oxide based catalyst that has a cerium oxide content of at least 60 wt %, wherein the cerium oxide based catalyst is at least one catalyst selected from the group consisting of:
 a composition comprising cerium oxide and at least one oxide of another rare earth,
 a composition comprising cerium oxide and at least one compound of another rare earth, a cerium composite oxide comprising at least cerium oxide, silicon oxide, titanium oxide and at least one oxide of another rare earth, and/or a composition comprising cerium oxide, zirconium oxide and at least one oxide of another rare earth; and wherein the cerium oxide based catalyst at least includes an oxide of a rare earth of one of praseodymium oxide and/or lanthanum oxide, wherein the cerium oxide based catalyst is used as such.

2. A method according to claim 1, wherein cycloalkane is selected from the group consisting of cyclopentane, cyclohexane, cycloheptane, and cyclooctane.

3. A method according to claim 2, wherein the cycloalkane is cyclohexane, the alcohol is cyclohexanol and the ketone is cyclohexanone.

4. A method according to claim 1, wherein the amount of catalyst is from 0.01 wt % to 10 wt. based on the total weight of the reaction medium.

5. A method to produce adipic acid, comprising:
oxidizing liquid cyclohexane by reaction with oxygen gas to produce cyclohexane hydroperoxide,
decomposing the cyclohexane hydroperoxide into a mixture of cyclohexanol and cyclohexanone, by using the cyclohexane hydroperoxide as the hydroperoxide compound in a method according to claim 1,
oxidizing, with nitric acid, the mixture of cyclohexanol and cyclohexanone to adipic acid, and extracting and purifying the adipic acid.

6. A method of producing polyamide, obtained by polycondensation from adipic acid produced by the method of claim 5, and hexamethylenediamine, comprising the following steps:

mixing adipic acid produced by the method of claim 5 with hexamethylenediamine, to produce hexamethylenediammonium adipate, and
heatingan aqueous solution of the hexamethylenediammonium adipate.

7. The method according to claim 1, wherein the cerium oxide based catalyst has a nano-rod nanostructure.

8. The method according to claim 1, wherein the cerium oxide based catalyst is a composition comprising cerium oxide and at least one oxide of another rare earth.

9. The method according to claim 1, wherein the cerium oxide based catalyst is a composition comprising cerium oxide and at least one compound of another rare earth.

10. The method according to claim 1, wherein the cerium oxide based catalyst is a cerium composite oxide comprising at least cerium oxide, silicon oxide, titanium oxide and at least one oxide of another rare earth.

11. The method according to claim 1, wherein the contacting of the cycloalkane with the cyclohexyl hydroperoxide compound in the presence of at least the cerium oxide based catalyst does not include an addition of any additional oxidizing agent selected from group consisting of pure oxygen, air, oxygen-enriched air, oxygen-depleted air, oxygen diluted with an inert gas, or a combination thereof.

12. The method according to claim 11, wherein the contacting of the cycloalkane with the cyclohexyl hydroperoxide compound in the presence of at least the cerium oxide based catalyst is conducted in the presence of a nitrogen overpressure.

* * * * *